United States Patent
Koob

(10) Patent No.: US 9,446,142 B2
(45) Date of Patent: Sep. 20, 2016

(54) POLYMER CHELATOR CONJUGATES

(71) Applicant: MiMedx Group, Inc., Kennesaw, GA (US)

(72) Inventor: Thomas J. Koob, Kennesaw, GA (US)

(73) Assignee: MiMedx Group, Inc., Marietta, GA (US)

( * ) Notice: Subject to any disclaimer, the term of this patent is extended or adjusted under 35 U.S.C. 154(b) by 291 days.

(21) Appl. No.: 13/903,878

(22) Filed: May 28, 2013

(65) Prior Publication Data

US 2014/0356451 A1    Dec. 4, 2014

(51) Int. Cl.
  *A61K 35/12*    (2015.01)
  *A61K 47/48*    (2006.01)

(52) U.S. Cl.
  CPC ... *A61K 47/48292* (2013.01); *A61K 47/48776* (2013.01)

(58) Field of Classification Search
  None
  See application file for complete search history.

(56) References Cited

U.S. PATENT DOCUMENTS

| | | | |
|---|---|---|---|
| 4,703,108 A | 10/1987 | Silver et al. | |
| 4,847,049 A | 7/1989 | Yamamoto | |
| 5,118,867 A | 6/1992 | Bahrmann et al. | |
| 5,284,655 A | 2/1994 | Bogdansky et al. | |
| 5,541,232 A | 7/1996 | Howell et al. | |
| RE35,748 E | 3/1998 | Luck et al. | |
| 5,807,581 A | 9/1998 | Rosenblatt et al. | |
| 6,030,635 A | 2/2000 | Gertzman et al. | |
| 6,129,757 A | 10/2000 | Weadock | |
| 6,166,184 A | 12/2000 | Hendriks et al. | |
| 6,503,244 B2 | 1/2003 | Hayman | |
| 6,565,960 B2 | 5/2003 | Koob et al. | |
| 6,716,895 B1 | 4/2004 | Terry | |
| 6,821,530 B2 | 11/2004 | Koob et al. | |
| 6,936,271 B1 | 8/2005 | Oliver et al. | |
| 7,101,857 B2 | 9/2006 | Sung et al. | |
| 7,311,904 B2 | 12/2007 | Hariri | |
| 7,311,905 B2 | 12/2007 | Hariri | |
| 7,901,455 B2 | 3/2011 | Koob et al. | |
| 8,067,044 B2 | 11/2011 | Henry et al. | |
| 8,153,162 B2 | 4/2012 | Tseng et al. | |
| 8,177,839 B2 | 5/2012 | Koob et al. | |
| 8,192,481 B2 | 6/2012 | King | |
| 8,367,148 B2 | 2/2013 | Greenhalgh et al. | |
| 2002/0019516 A1 | 2/2002 | Noff et al. | |
| 2002/0037940 A1 | 3/2002 | Koob et al. | |
| 2002/0123141 A1 | 9/2002 | Hariri | |
| 2002/0160510 A1 | 10/2002 | Hariri | |
| 2003/0032179 A1 | 2/2003 | Hariri | |
| 2003/0187515 A1 | 10/2003 | Hariri et al. | |
| 2003/0204023 A1 | 10/2003 | Koob et al. | |
| 2004/0028711 A1 | 2/2004 | Uchida et al. | |
| 2004/0048796 A1 | 3/2004 | Hariri et al. | |
| 2005/0142161 A1 | 6/2005 | Freeman et al. | |
| 2006/0140913 A1 | 6/2006 | Bhatia | |
| 2006/0210532 A1 | 9/2006 | Carmeliet et al. | |
| 2007/0020225 A1* | 1/2007 | Abramson et al. | 424/78.27 |
| 2007/0160573 A1 | 7/2007 | Gengrinovitch | |
| 2007/0202189 A1 | 8/2007 | Ahlfors | |
| 2007/0248575 A1 | 10/2007 | Connor et al. | |
| 2008/0020012 A1 | 1/2008 | Ju et al. | |
| 2008/0046095 A1 | 2/2008 | Daniel | |
| 2008/0050347 A1 | 2/2008 | Ichim | |
| 2008/0131966 A1 | 6/2008 | Hariri | |
| 2008/0161917 A1 | 7/2008 | Koob et al. | |
| 2008/0181935 A1* | 7/2008 | Bhatia et al. | 424/443 |
| 2008/0200992 A1 | 8/2008 | Koob et al. | |
| 2008/0233552 A1 | 9/2008 | Ma et al. | |
| 2009/0012629 A1 | 1/2009 | Yao et al. | |
| 2009/0036996 A1 | 2/2009 | Roeber | |
| 2009/0053290 A1 | 2/2009 | Sand et al. | |
| 2009/0092664 A1 | 4/2009 | Mumper et al. | |
| 2009/0142831 A1 | 6/2009 | Hariri | |
| 2009/0216233 A1 | 8/2009 | Wiedrich et al. | |
| 2009/0287308 A1 | 11/2009 | Davis et al. | |
| 2009/0291891 A1 | 11/2009 | Neufeld | |
| 2010/0028849 A1 | 2/2010 | Shelby et al. | |
| 2010/0094318 A1 | 4/2010 | Li et al. | |
| 2010/0094404 A1 | 4/2010 | Greenhalgh et al. | |
| 2010/0104539 A1 | 4/2010 | Daniel et al. | |
| 2010/0136114 A1 | 6/2010 | Mao | |
| 2010/0143312 A1 | 6/2010 | Hariri et al. | |
| 2010/0178297 A1 | 7/2010 | Carmeliet et al. | |
| 2010/0209408 A1 | 8/2010 | Livesey et al. | |
| 2010/0260847 A1 | 10/2010 | Hariri | |

(Continued)

FOREIGN PATENT DOCUMENTS

| | | |
|---|---|---|
| CN | 101433556 | 5/2009 |
| EP | 0 167 263 | 1/1986 |

(Continued)

OTHER PUBLICATIONS

U.S. Appl. No. 13/984,842, filed Feb. 13, 2012, Morse et al.
U.S. Appl. No. 13/815,775, filed Mar. 15, 2013, Koob.
U.S. Appl. No. 13/815,834, filed Mar. 15, 2013, Koob.
U.S. Appl. No. 13/815,873, filed Mar. 15, 2013, Brown et al.
U.S. Appl. No. 13/860,473, filed Apr. 10, 2013, Koob.
U.S. Appl. No. 13/903,878, filed May 28, 2013, Koob.
U.S. Appl. No. 61/543,995, filed Oct. 6, 2011, Daniel et al.
U.S. Appl. No. 61/683,698, filed Aug. 15, 2012, Koob et al.

(Continued)

*Primary Examiner* — Chris R Tate
*Assistant Examiner* — Douglas F White
(74) *Attorney, Agent, or Firm* — Foley & Lardner LLP

(57) ABSTRACT

Provided herein are biocompatible polymer conjugates comprising a biologically compatible polymer covalently bound to a biologically compatible chelator moiety, which in turn are optionally bound, reversibly, to pharmacologically active metal ions. The biologically compatible polymer may comprise of modified placental tissue grafts composed of at least one membrane, capable of recruiting stem cells in vivo and in vitro.

14 Claims, 7 Drawing Sheets

(56) References Cited

U.S. PATENT DOCUMENTS

| | | |
|---|---|---|
| 2010/0291182 A1 | 11/2010 | Palasis et al. |
| 2010/0317677 A1 | 12/2010 | Hassel et al. |
| 2011/0044997 A1 | 2/2011 | Rankin et al. |
| 2011/0097379 A1 | 4/2011 | Yoo et al. |
| 2011/0189301 A1 | 8/2011 | Yang et al. |
| 2011/0206776 A1 | 8/2011 | Tom et al. |
| 2011/0282447 A1 | 11/2011 | Niu et al. |
| 2011/0282448 A1 | 11/2011 | Paulos et al. |
| 2011/0307059 A1 | 12/2011 | Young et al. |
| 2012/0010708 A1 | 1/2012 | Young et al. |
| 2012/0078378 A1 | 3/2012 | Daniel et al. |
| 2012/0135045 A1 | 5/2012 | Nixon et al. |
| 2012/0189571 A1 | 7/2012 | Sengupta et al. |
| 2012/0189586 A1 | 7/2012 | Harrell |
| 2012/0282348 A1 | 11/2012 | Yates et al. |
| 2012/0294910 A1 | 11/2012 | Daniel et al. |
| 2013/0202676 A1 | 8/2013 | Koob et al. |
| 2013/0230561 A1 | 9/2013 | Daniel et al. |
| 2014/0342015 A1* | 11/2014 | Murphy et al. ............... 424/582 |

FOREIGN PATENT DOCUMENTS

| | | |
|---|---|---|
| EP | 0 431 164 A1 | 6/1991 |
| EP | 0 431 479 A1 | 6/1991 |
| EP | 0 506 207 B1 | 9/1992 |
| KR | 2001/100588 | 11/2001 |
| WO | WO-87/00062 A1 | 1/1987 |
| WO | WO-88/03805 A1 | 6/1988 |
| WO | WO-98/31404 | 7/1998 |
| WO | WO-01/00101 | 1/2001 |
| WO | WO-01/00151 A1 | 1/2001 |
| WO | WO-2007/083984 A1 | 7/2007 |
| WO | WO-2012/065937 A1 | 5/2012 |
| WO | WO-2012/069559 A1 | 5/2012 |
| WO | WO-2012/112417 A2 | 8/2012 |

OTHER PUBLICATIONS

U.S. Appl. No. 61/683,699, filed Aug. 15, 2012, Koob et al.
U.S. Appl. No. 61/683,700, filed Aug. 15, 2013, Daniel et al.
International Search Report and Written Opinion for PCT Patent Application No. PCT/US2012/024814 mailed Aug. 16, 2012.
International Preliminary Report on Patentability dated Feb. 14, 2013 in related PCT Patent Application No. PCT/US2012/024814.
International Search Report and Written Opinion dated Feb. 8, 2013 in related PCT Application No. PCT/US2012/0656722.
Hannallah et al., "Cerebrospinal Fluid Leaks Following Cervical Spine Surgery", J Bone Joint Surg Am, 2008;90(5):1101-1105.
Khan et al., "Postoperative management protocol for incidental dural tears during degenerative lumbar spin surgery: a review of 3,183 consecutive degenerative lumbar cases", Spine, 2006; 31(22)2609-2613.
Koob et al., "Mechanical and thermal properties of novel polymerized NDGA—gelatin hydrogels", Biomaterials, 2003; 24(7):1285-1292.
Koob et al., "Material properties of polymerized NDGA-collagen composite fibers: Development of biologically based tendon constructs", Biomaterials, 23(1) 203-212, 2002.
Kostova, "Platinum Complexes as Anticancer Agents", Recent Patents on Anti-Cancer Drug Discovery, 2006; 1(1):1-22.
Mayfield et al., "Watertight closure of spinal dura mater: Technical note", Journal of Neurosurgery, 1975; 43(5):639-640.
PCT International Search Report and Written Opinion dated Apr. 16, 2014 in PCT Patent Application No. PCT/US13/67622.
PCT International Search Report and Written Opinion dated Apr. 21, 2014 in PCT Patent Application No. PCT/US13/67623.
PCT International Search Report and Written Opinion dated Apr. 22, 2014 in PCT Patent Application No. PCT/US13/67618.
PCT International Search Report and Written Opinion dated Apr. 22, 2014 in PCT Patent Application No. PCT/US13/67620.
U.S. Appl. No. 13/815,736, filed Mar. 15, 2013, Koob.
Borkow et al., "Reducing the risk of skin pathologies in diabetics by using copper impregnated socks", Medical Hypotheses, 2009, 1-4, doi:10.1016/j.mehy.2009.02.050.
Konishi et al., In vivo anti-tumor effect through the controlled release of cisplatin from biodegradable gelatin hydrogel,: J. Controlled Release, 2003, 92(3):301-313.
Lu et al., "Molecular mechanisms and clinical applications of nordihydroguaiaretic acid (NDGA) and its derivatives: An update," Med. Sci. Monit., 2010, 16(5):RA93-RA100.
"MiMedx Group Announces Launch of EpiFixTM and Hiring of Vice President, Wound Care," Mimedx Press Release (2011).
Autiero et al., "Placental growth factor and its receptor, vascular endothelial growth factor receptor-1:novel targets for stimulation of ischemic tissue revascularization and inhibition of angiogenic and inflammatory disorders," J. Thromb. Haemo., (2003), 1:1356-1370.
Derwent Abstract for KR 200110588, original document published Nov. 2001.
EpiFix Product Brochure (2011).
Hattori et al., "Placental growth factor reconstitutes hematopoiesis by recruiting VEGFR1+ stem cells from bone-marrow microenvironment," Nat. Med., (2002), 8(8):841-849.
http://proxybiomedical.com/Images/ML005-01-Rev002.pdf (accessed on Jun. 5, 2014).
International Preliminary Report on Patentability issued on PCT/US13/67620, mailed Apr. 17, 2014.
MiMedx Press Release, "MiMedx Scientific Study is Electronically Published in the International Wound Journal", 2013.
Moussy et al., "Transport characteristics of a novel local drug delivery system using nordihydroguaiaretic acid (NDGA)-polymerized collagen fibers," Biotechnology Progress, (2007), 23(4):990-994.
PCT International Preliminary Report on Patentability dated Dec. 3, 2014 for PCT Patent Application No. PCT/US2013/067618.
PCT International Preliminary Report on Patentability dated Dec. 30, 2014 for PCT Patent Application No. PCT/US13/67622.
PCT International Preliminary Report on Patentability dated Nov. 10, 2014 for PCT Patent Application No. PCT/US2013/067623.
PCT International Search Report and Written Opinion dated Aug. 26, 2014 for PCT Patent Application No. PCT/US2014/033346.
PCT International Search Report and Written Opinion dated Dec. 29, 2014 for PCT Patent Application PCT/US2014/053270.
PCT International Search Report and Written Opinion dated Dec. 30, 2014 in PCT Patent Application No. PTC/US2014/054603.
Young Min Ju. A novel bio-stable 3D porous collagen scaffold for implantable biosensor; Ph.D. Dissertation 2008.
Ma, He-wei, et al. Recovery of platinum(IV) and palladium(II) by bayberry tannin immobilized collagen fiber membrane from water solution. Journal of Membrane Science 278,373-380 (2006).

* cited by examiner

POLYMER CHELATOR CONJUGATES

FIELD OF THE INVENTION

This invention relates to a biocompatible polymer conjugate comprising a biologically compatible polymer and a biologically compatible chelator moiety covalently bound thereto. This invention further comprises said conjugate having pharmacologically active metal ions reversibly bound thereto. In one embodiment, the biologically compatible polymer is collagen.

STATE OF THE ART

Koob et al. have described methods of producing nordihydroguaiaretic acid (NDGA) polymerized and cross-linked collagen fibers for various biomedical applications, some with tensile strengths similar to that of natural tendon (e.g., about 91 MPa). See, for example, Koob and Hernandez, *Material properties of polymerized NDGA-collagen composite fibers: development of biologically based tendon constructs*, Biomaterials 2002 January; 23 (1): 203-12; and U.S. Pat. No. 6,565,960, the contents of which are hereby incorporated by reference as if recited in full herein.

Cross-linked polymers such as collagen possess different properties as compared to non-cross-linked polymer including a substantially longer in vivo residence time. In some cases, a long in vivo residence time is undesirable as a shorter clearance time for the polymer releasing therapeutic metal ions is desired. In some cases, a mixture of cross-linked and non-cross-linked polymers provide for a compatible mix of properties.

SUMMARY OF THE INVENTION

Thus, this invention provides a biologically compatible polymer-chelator conjugate comprising a biologically compatible polymer and one or more chelating moieties, wherein the chelating moieties are covalently bound to the polymer but the polymer is otherwise substantially non-cross-linked by the chelating moiety. That is to say that the chelating agent either minimally or does not participate in cross-linking the polymer. Preferably, at least 80% of the chelating moieties of such conjugates do not cross-linked the polymer. More preferably, at least 90% and even more preferably at least 95% of the chelator moieties do not cross-link with the polymer. In one embodiment, none of the chelating moieties provide either intra-polymeric or extra-polymeric cross-linking. It is understood, however, that the polymer employed is optionally cross-linked with a non-chelating cross-linking agent.

The chelating moiety can be any moiety with functional groups pendent thereto which are suitable for reversibly binding biologically compatible and pharmacologically active metal ions. Examples of such biologically compatible and pharmacologically active metal ions include, without limitation, ions of silver, copper, or a metallic ionic anti-tumor agent. Preferably, the anti-tumor agent is ionic platinum.

BRIEF DESCRIPTION OF THE DRAWINGS

The accompanying drawings, which are incorporated in and constitute a part of this specification, illustrate several aspects described below.

In FIG. 1, the release rates of the metal ions from a polymer-chelating agent conjugate containing different non-cross-linking chelating agents (moieties) are illustrated. The release rates from these two different chelating agents are selected to overlap so as to provide a sustained release of the metal ion over time. In FIG. 2, the release rates of the metal ions from similar two conjugates are illustrated. In this case, the chelating moieties of the conjugates are selected so that their release rates do not to overlap. This results in release of a first bolus of metal ion release followed by release of a second bolus of metal ion.

DETAILED DESCRIPTION OF THE INVENTION

Figure 1:
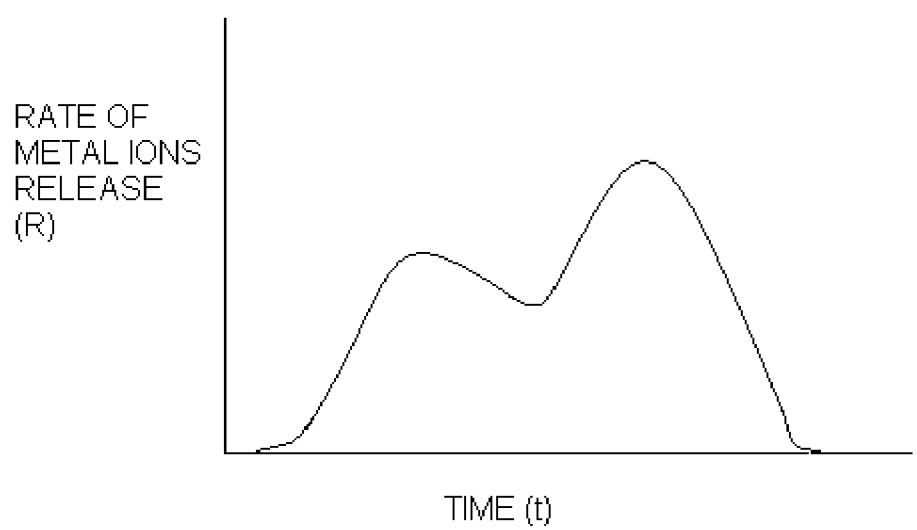
FIGS. 1 and 2 illustrate different binary release patterns of metallic ions from a composition comprising a mixture of substantailly non-cross-linked polymer-chelating agent conjugates using different chelating moieties.

This invention relates to substantially non-cross-linked polymer chelator conjugates. Various embodiments of this invention are described below.

Definitions

All numerical designations, e.g., pH, temperature, time, concentration, and weight, including ranges of each thereof, are approximations that typically may be varied (+) or (−) by increments of 0.1, 1.0, or 10.0, as appropriate. All numerical designations may be understood as preceded by the term "about".

As used herein, the singular forms "a", "an" and "the" are intended to include the plural forms as well, unless the context clearly indicates otherwise.

The term "comprising" means any recited elements are necessarily included and other elements may optionally be included. "Consisting essentially of" means any recited elements are necessarily included, elements that would materially affect the basic and novel characteristics of the listed elements are excluded, and other elements may optionally be included. "Consisting of" means that all elements other than those listed are excluded. Embodiments defined by each of these terms are within the scope of this invention.

"$C_m$" when placed before a group refers to that group containing m carbon atom(s).

"Alkyl" refers to a hydrocarbyl radical, preferably monovalent, containing 1-12 carbon atoms. Non limiting examples of alkyl includes methyl, ethyl, propyl, isopropyl, butyl, isobutyl, tertiary butyl, and the like.

"Cycloalkyl" refers to a cyclic hydrocarbyl radical, preferably, monovalent, containing 3-10 carbon atoms and includes bicyclic radicals. Non-limiting examples of cycloalkyl include cycloproyl, cyclobutyl, cyclopentyl, cyclohexyl, and the like.

"Aryl" refers to a aromatic hydrocarbyl mono-, bi-, or tricyclic ring.

"Heteroayl" refers to a an aryl ring containing 1-5 ring heteroatoms selected from nitrogen, oxygen, sulfur, and appropriate oxxideized forms thereof.

"Aldehyde" refers to a compound of formula O=C(H)—R wherein R is selected from the group consisting a chelating moiety connected to the aldehyde optionally through a linker moiety. When a linker is employed, the aldehyde is represented by the formula R-L-aldehyde and L is the linker.

"Isocyanate" refers to a compound of formula O=N=C-L-R where R is as defined above and L is a bond or a linker moiety.

"Di-alpha-diazo pyruvate" refers to a compound of formula R-L-C(O)C(O)N$_2$, wherein R and L are defined as above.

The term "subject" or "patient" as used herein refers to any vertebrate organism including, but not limited to, mammalian subjects such as humans, farm animals, domesticated pets and the like.

The term "amnion" as used herein includes amniotic membrane where the intermediate tissue layer is intact or has been substantially removed.

The term "biocompatible" as used herein refers to a material that is suitable for implantation or injection into a subject. In various aspects, a biocompatible material does not cause toxic or injurious effects once implanted in the subject.

The term "modified placental tissue" refers to any and all components of placental tissue including whole placental tissue that has been modified by cleaning, disinfecting, and/or segmenting the tissue as well as to separated components of placental tissue such as amnion, chorion, the umbilical cord, and the like. Modified tissue may maintain cellular layers, such as the epithelial layer and/or the fibroblast layer. Modified placental tissue may include further modification, such as lamination of one or more layers of placental tissue, micronization of placental tissue, chemisorption or physisorption of small molecules, proteins (e.g. growth factors, antibodies), nucleic acids (e.g. aptamers), polymers, or other substances.

The term "sufficient amount" refers to an amount of a modified placental tissue that is sufficient to provoke stem cell recruitment proximate to or on the modified placental tissue over time, either in vivo or in vitro. The "sufficient amount" of a modified placental tissue will vary depending on a variety of factors, such as but not limited to, the type and/or amount of placental tissue used, the type and/or size of the intended organ and/or body part to be treated, the severity of the disease or injury to the organ and/or body part to be treated and the administration route. The determination of a "sufficient amount" can be made by one of ordinary skill in the art based on the disclosure provided herein.

The term "stem cell recruiting factors" refers to any and all factors that are capable of recruiting stem cells and causing them to migrate towards a source of such factors. Non-limiting examples of stem cell recruiting factors may be one or more CC chemokines, CXC chemokines, C chemokines, or $CX_3C$ chemokines.

The term "stem cell recruitment" refers to direct or indirect chemotaxis of stem cells to a modified placental tissue. The recruitment may be direct, wherein stem cell recruiting factors (e.g. chemokines, which induce cell chemotaxis) in a modified placental tissue are released from the placental tissue and induce stem cells to migrate towards the placental tissue. In one aspect, the recruitment may be indirect, wherein stem cell recruiting factors in a modified placental tissue are released from the placental tissue which induce nearby cells to release factors (e.g. chemokines), that in turn induce stem cells to migrate towards the placental tissue. Still further, stem cell recruitment may embody both direct and indirect factors.

In one embodiment, placental tissue may be modified as described in U.S. Ser. No. 61/683,698, including cleaning, separation of the amnion and chorion, removal or maintenance of the epithelial cell layer, decontamination, and dehydration. Dehydration may be accomplished using the drying apparatus as described in U.S. Ser. No. 61/683,698. Both of which applications are incorporated herein by reference in their entirety. Each aspect of that process produces modified placental tissue for the purposes of this invention whether used alone or in combination. However, it is preferred that the modified placental tissue include at least the steps of cleaning and decontamination. As such, modified placental tissue preferably comprises placental tissue which has been cleaned and decontaminated and also includes placental tissue which has undergone one or more of separation of the amnion and chorion, removal of the epithelial cell layer, and dehydration.

In some embodiments of the present technology, the modified placental tissue is selected from amnion, chorion, or both amnion and chorion. In preferred embodiments, modified placental tissue does not include the umbilical cord.

Modified placental tissue can also be formed into layers which may be dried separately and laminated together or dried together to form multi-layer laminates. Modified placental tissue may also be micronized into particles of a variety of sizes. Micronized placental tissue may be sandwiched between one or more layers of a multilayer laminate, or on top of a laminate. Micronized placental tissue may also be added to single layer of modified placental tissue. See, for example, U.S. Provisional Application Ser. No. 61/543,995 which is incorporated herein by reference in its entirety.

Polymers

Suitable polymers include those that are known in the art and are capable of forming chelator conjugates as described herein. Preferred biocompatible polymers useful in this invention include biodegradable polymers.

Suitable polymers include, without limitation, naturally-occurring polymers, synthetic polymers or mixtures thereof. In one embodiment, the polymer includes collagen or placental tissue e.g. amnion or chorion containing collagen. Other examples of naturally-occurring biocompatible polymers include, but are not limited to, hylauronic acid, fibrin, fibrous or globular proteins, complex carbohydrates, glycosaminoglycans, such as, or mixtures thereof. Thus, in one embodiment, the polymer may include collagens of all types, elastin, laminin, hyaluronic acid, alginic acid, desmin, versican, fibrin, fibronectin, vitronectin, albumin, and the like. Exemplary synthetic biocompatible polymers include, but are not limited to, polyoxyalkylenes (e.g., polyoxyethylene, polyoxypropylene, copolymers of oxyethylene and oxypropylene, and the like), polyethylene glycol, polymethylene glycol, polytrimethylene glycols, polyvinylpyrrolidones, caprolactones, 2-hydroxyethyl methacrylate (HEMA), silicone such as Nusil MED-6215 or other silicone suitable for implantation, poly(epsilon-caprolactone) dimethylacrylate, polysulfone, (poly)methyl methacrylate (PMMA), soluble Teflon-AF, poly ethylene teraphthalate (PET, Dacron), Nylon, polyvinyl alcohol, polyurethane, hydroxyapatite, and the like and mixtures thereof. Such polymers preferably have a number average molecular weight of at least about 10,000 and more preferably from about 10,000 to about 1,000,000. On some embodiments, these polymers preferably have a weight average molecular weight of at least 10,000 and more preferably from about 10,000 to about 100,000. The polymers described herein can be either cross-linked with non-chelating agents or non-cross-linked. Common non-chelating cross-linking agents include carbodimides, diisothiocyanates, dicarboxylic acids, diamines and the like.

In some embodiments, the biocompatible polymers are water soluble polymers and are sometimes referred to as hydrophilic polymers. Water solubility can be achieved incorporating a sufficient number of oxygen (or less frequently nitrogen) atoms available for forming hydrogen bonds in aqueous solution. Hydrophilic polymers include, without limitation, polyoxyethylene, polyethylene glycol, polymethylene glycol, polytrimethylene glycols, polyvinylpyrrolidones, or derivatives thereof. The polymers are preferably linear or only slightly branched (i.e., having only about 2-10 significant free ends), and will not be substantially cross-linked. Other suitable polymers include polyoxyethylene-polyoxypropylene block polymers and copolymers.

Polyoxyethylene-polyoxypropylene block polymers having an ethylene diamine nucleus (and thus having four ends) are also available and may be used in the practice of the invention. Hydrophilic polymers can also include naturally occurring polymers such as proteins (e.g., and without limitation, a collagen), starch, cellulose, and the like.

All suitable polymers are biocompatible, and preferably non-toxic and non-inflammatory when administered in vivo, and will more preferably be degradable in vivo with a degradation time of at least several months.

The polymers of this invention have at least one and preferably up to 1000 reactive functionalities which are complementary to the reaction functionalities on the precursor chelator compound. Typically, the complementary reactive functionality is present on the polymer such as reactive functionalities found in collagen, hylauronic acid, and the like or can be introduced onto the polymer by conventional chemical synthetic techniques well known to the skilled artisan. Exemplary functionalities include, without limitation, amine, carboxylic acid, hydrazine, hydrazone, azide, isocyanate, isothiocyanate, alkoxyamine, aldehyde, epoxy, nitrile, maleimide, halo, hydroxyl, thiol or a combination thereof. Preferably, the reactive functional group is selected from the amine or carboxylic acid. Complementary functionalities include those that react with each other to form a covalent bond. Examples include isocyanates with amines and hydroxyl groups to form a urea or carbamate linkage, carboxylic acids and amines which form amides, and the like. The following table illustrated some common complementary reactive groups one of which is found on the precursor chelating moiety (first reactive functionality) and the other on the polymer (second reactive functionality).

| First reactive functionality | Second reactive functionality | Covalent Bond formed |
| --- | --- | --- |
| Amine | Carboxyl | Amide |
| Hydroxyl | Halide | Ether |
| Isocyanate | Amine | Urea |
| Isocyanate | Hydroxyl | Carbamate |
| Carboxyl | Amine | Amide |
| Thioisocyanate | Hydroxyl | Thiocarbamate |

The polymers of the invention can be functionalized, for example, by introducing an amine-functional monomer, either pendant or terminal to the polymer. A suitable method for imparting a pendant amine functionality to the polymer is to use a monomer containing a pendant amine functionality. Suitable monomers containing a pendant amine functionality include 2-aminoethylacrylate, 2-aminoethylmethacrylate, 2-aminoethylacrylamide, 2-aminoethylmethacrylamide, dimethylaminoethylmethacryl, aminopropyl (meth)acrylamide and the like. When a monomer containing a pendant amine functionality is used, the resulting polymer may contain one or more pendant amine groups. Preferably, the pendant amine functionality which is imparted to the polymer is a terminal pendant amine functionality. Terminal pendant amine functionality can be imparted to a polymer by using one or more compounds which, when they function as a chain transfer agent, have a pendant amine group. Preferred compounds for imparting terminal amine functionality are amine-thiols, e.g., N-butylaminoethanethiol, N,N-diethylaminoethanethiol and salts thereof.

Likewise, the polymers of the invention can be functionalized, for example, by introducing a carboxylic acid-functional monomer. Preferred acid monomers are carboxylic acids or their derivatives, including, but not limited to, monounsaturated monocarboxylic acid, monounsaturated dicarboxylic acid, anhydrides or alcohol derived mono- or di-esters. Upon reaction with the polymer, e.g., a polyolefin, the monounsaturation of the monounsaturated carboxylic reactant becomes saturated. Exemplary monounsaturated carboxylic reactants include fumaric acid, itaconic acid, maleic acid, maleic anhydride, chloromaleic acid, chloromaleic anhydride, acrylic acid, methacrylic acid, crotonic acid, cinnamic acid, and lower alkyl acid esters, such as methyl maleate, ethyl fumarate, and methyl fumarate. In other embodiments, polymer containing anhydride or ester functionality can be converted by well known hydrolysis methods to acid.

Chelators

A variety of chelators well known for binding various pharmacologically active metal ions, such as, ions of copper, silver, and platinum, are useful in; preferably such chelators are biocompatible.

Suitable chelators preferably comprise one or more $C_2$-$C_{10}$ alkyl or heteroalkyl, $C_6$-$C_{10}$ aryl $C_3$-$C_{10}$ heteroaryl, or $C_5$-$C_{10}$ cycloalkyl groups substituted with at least two, adjacent (or 1,2 substitued) hydroxy, alkoxy, amino, alkylamino, dialkylamino, mercapto, thioalkyl groups, which alkyl or heteroalkyl, aryl, heteroaryl, or cycloalkyl groups are attached via a linker, or a bond and a functional joining group, to the biocompatible polymer.

The term "chelator precursor compound" refers to the chelator prior to reaction with the polymer. The precursor compound contains a reactive functionality which reacts with a complementary functionality on the polymer to form a covalent bond. The resulting chelating moiety is referred to as the "chelator" and is defined above. The reactive functional groups on the chelator precursor compounds form a stable covalent bond when coupled with the complementary reactive functional group on the polymer. Such stable covalent bonds include by way of example esters, ethers, amides (—CONH—, —NHCO—, —N(alkyl)CO— or CO—N(alkyl)-), carbamates, urea, carbonate, thiocarbonate, thiourea, carbamate, and urethane bonds, as well as any other well known covalent bonds. Reactive functional groups either on the chelator precursor compound or the polymer include those such as amino, hydroxy, mercapto, and carboxylic acid, carboxylate esters, isocyanate, and other well known functional groups that can be chemically bonded following art known methods to a complementary reactive functional group on the polymer as utilized herein. The group X on the chelator precursor compound is selected from the group consisting of H or a complimentary reactive functional group. It is understood that when X is a complimentary functional group the other functional groups on the compound may need to be blocked or protected using conventional methods and protecting groups In one embodiment, the chelating agent comprises a 1,2-benzoquinone and/or a 1,2-dihydroxy phenyl moiety. In another embodiment, the chelating moiety is derived from a precursor compound selected from the group consisting of nordihydroguaiaretic acid (NDGA), 3,4-dyhydroxyphenylalanine, dopamine, 3,4-dihydroxybenzaldehyde, and 3,4-dihydroxybenzoic acid.

In one embodiment, the chelating agent is derived from a precursor compound which can both react with and forma a covalent bond to collagen and reversibly bind the antimicrobial metal ion. Preferably, the precursor compound is selected from the group consisting of:

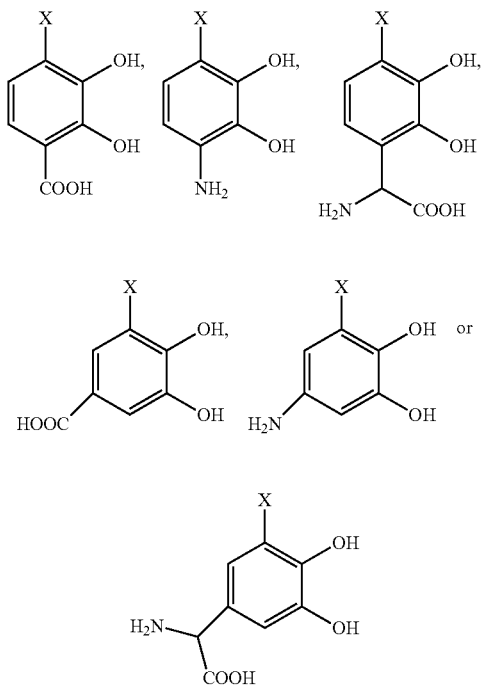

wherein X is H or a complimentary reactive functional group, such that when X is a complimentary reactive functional group, the other functional groups on the molecule are protected.

In one embodiment, the precursor compound is:

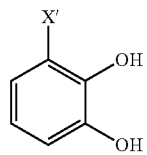

where X' is a complimentary reactive functional group, such that the hydroxyl groups on the molecule are optionally protected.

Preferable chelating agents used are derived from naturally occurring compounds such as dopamine and L-dopa.

After reaction, the chelator is sometimes referred to a chelating agent or as a chelating moiety.

Pharmacologically Active Metal Ions

Suitable pharmacologically active metals are known in the art. In one embodiment, the pharmacologically active metal ion is an antimicrobial agent. Antimicrobial metals include, without limitation, silver, gold, platinum and palladium. In one embodiment, the metal ion is silver. In another embodiment, the silver comprises ionic silver selected from the group consisting of silver (I) and/or silver (II). In other embodiments, the ionic silver may be bound to two or more nitrogen, and/or sulfur and/or oxygen atoms. In another embodiment, the ionic silver is the dissociation product of silver chloride, silver phosphate, silver sulfate, silver acetate, silver nitrate, silver fluoride, silver iodide, silver lactate, silver benzoate, silver bromide, silver carbonate, silver citrate, silver iodate, silver laurate, silver oxide, silver palmitate, silver protein, silver imidazolate, arglaes, colloidal silver, silver crystals, such as silver nanocrystals, silver plating, and/or silver sulfonamides, such as, e.g., such as silver sulfadiazine. In another embodiment, the silver incorporated into the construct is present in an amount of between about 0.1% to about 30%.

In one embodiment, the pharmacologically active metal ion is an antifungal agent. Antifungal metals include, without limitation, copper, iron, manganese, and zinc. In one embodiment, the metal ion is ionic copper. In another embodiment the ionic copper incorporated into the construct is bound to two or more nitrogen, and/or sulfur and/or oxygen atoms. Such chelators can include quinone group and/or a catechol group present in the collagen construct. In yet another embodiment of the invention, the ionic copper incorporated into the construct is bound to a basic nitrogen atom, nonlimiting examples of which include amino, or mono- or di-alkylated amino, and imidazole. In other embodiments, the copper may be bound to two or more nitrogen, and/or sulfur and/or oxygen atoms. In certain aspects, the ionic copper is selected from the group consisting of copper chloride, copper phosphate, copper sulfate, copper acetate, copper nitrate, copper fluoride, copper iodide, copper lactate, copper benzoate, copper bromide, copper carbonate, copper citrate, copper iodate, copper laurate, copper oxide, copper palmitate, copper protein, copper proteinate, copper imidazolate, colloidal copper, copper alloys, copper crystals, including copper nanocrystals, copper plating, and/or copper sulfonamides.

The copper and silver chelates of this invention can be prepared by reacting the polymer constructs with water soluble and water stable salts of copper and silver, such as their acetate salts. Methods for making chelates of other metals will be apparent to the skilled artisan upon reading this disclosure. In one embodiment, the collagen construct can be incubated with an appropriate salt of the pharmacologically active metal, for example, in water, to provide a collagen construct of this invention that comprises a pharmacologically active metal. For example, the polymer construct in an aqueous media is reacted with a silver salt, such as silver acetate to precipitate the silver-polymer construct.

In one embodiment, a metal salts, such as diamine salts with a functionalized polymer, such as a carboxylic acid functionalized polymer, so that the metal is covalently bonded to the polymer construct.

In one embodiment, the pharmacologically active metal is an anticancer agent. Anticancer metals include, without limitation, platinum, ruthenium, osmium and cobalt. In one embodiment, the metal ion is ionic platinum. In one embodiment, the platinum comprises platinum (II) and/or platinum (IV). In another embodiment, the platinum comprises a compound selected from the group of cis-platin,

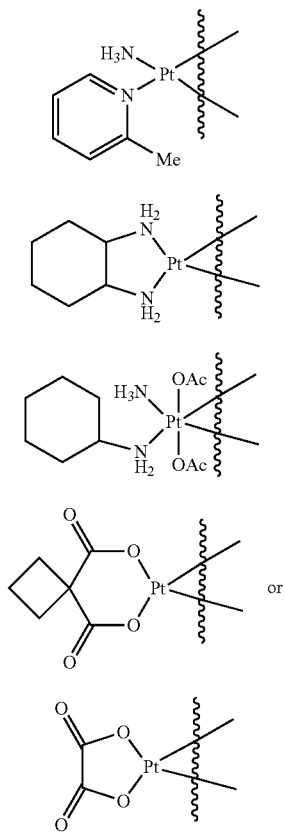

wherein

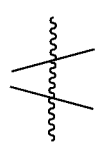

denotes binding to the chelator.

The chelated polymer-Pt constructs of this invention are prepared by contacting appropriate Pt salts, preferably, Pt(II) salts with a functionalized polymer of this invention. Preferably, the Pt salt is a cis diamino Pt(II) dichloro or, yet more preferably, a cis diamino Pt(II) diaqua salt. An illustrative and non-limiting example is shown below:

Step A

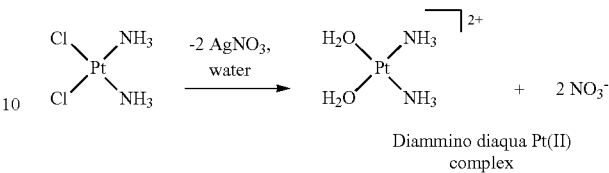

Diammino diaqua Pt(II) complex

Step B

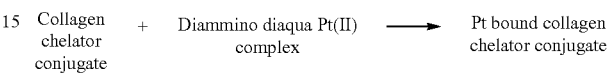

Figure 2:
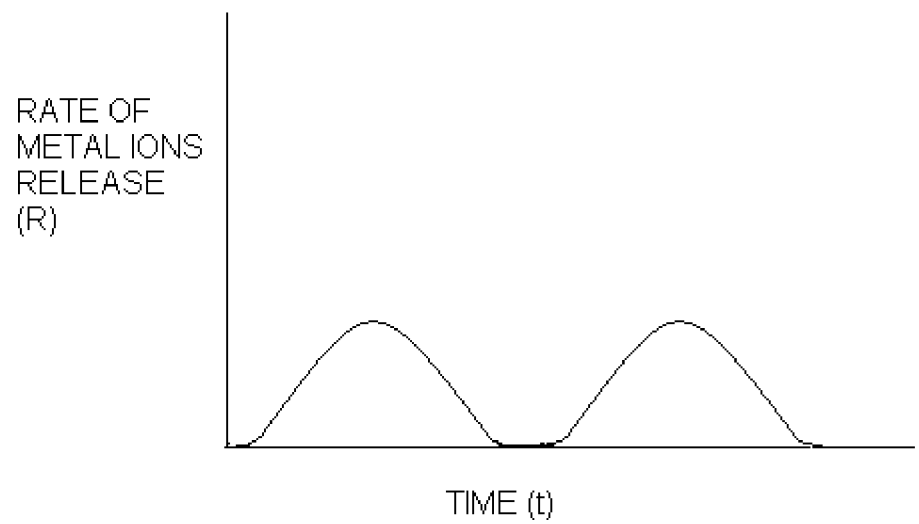

Excess Pt salts, not bound to the polymers of this invention, can be removed by complexed with a resin, such as Chelex. A polymer-Pt(II) construct can be converted to the corresponding Pt(IV) construct by oxidation, for example with $H_2O_2$. FIGS. 1 and 2 illustrate the use of different conjugates in a manner where the release rates of the conjugates overlap (FIG. 1) so as to provide a continuous release of the metal ion whereas FIG. 2 illustrates the use of different conjugates in a manner where the release rates do not overlap so as to provide two separate releases (bolus) of metal ion.

Polymer Conjugates

The polymer constructs of this invention are described below using collagen as an exemplary polymer. It is understood, however, that polymers other than collagen, such as those described herein, can be utilized in place of collagen. Accordingly, exemplary biocompatible collagen conjugates can be formed in the shape of, for example, patches, such as wound bed patches, muscle or organ patches, cardiac patches, hernia patches, skin patches, burn treatment patches, and skin/tissue repair patches; cuffs; blood vessel (artery, vein, and the like) repair material; valve replacements or valve repair material; auto-graft material; allo-graft material such as amnion and chorion; xenograft material; nerve guides; tubes; tendon sleeves, such as sleeves that can reside about repairing tendon to prevent or inhibit adhesions; indwelling tubes for delivery of antimicrobial agents; ducts, such as lymphatic, hepatic, pancreatic and cystic ducts; tubes, such as ureter and urethra tubes; collagen fiber; collagen gel; sutures; cords; twisted cords; ligament and/or tendon prosthesis; cables; braids; ribbons; staples; rivets; sponges; and the like. Further examples and description of devices are described in U.S. Pat. No. 7,901,455; U.S. Patent Application Publication Nos. 2008/0161917, 2008/0188933, 2008/0200992, 2009/0216233, 2009/0287308, 2010/0094318, and 2010/0094404; U.S. patent application Ser. Nos. 13/153,665 and 13/105,353; and U.S. Provisional Patent Application No. 61/450,179, which are incorporated herein by reference.

The conjugates of the present invention can be dry or partially hydrated. The term "dry" as used herein means the construct has a moisture content of less than about 5% by weight of the construct. The term "partially hydrated" as used herein means that the construct has a moisture content that is less than about 50%, typically less than about 75% of the moisture content at full hydration, measured ex vivo after 24 hours in a saline bath at ambient conditions. Thus, the construct can have a moisture content of less than about 25% by weight of the construct, such as less than about 15% by weight of the construct. In certain embodiments, the construct comprises at least one dry manufactured collagen fiber which can be in the form of a patch, an implant such as an implantable patch, wound around a device such as a medical device, and the like.

The term "patch" refers to a piece or segment of biomaterial that can be placed on and/or affixed to target anatomical structure, typically soft tissue, to treat, protect, repair and/or reinforce a target site. The patch can be any geometric shape but is typically substantially planar and may, in position, conform to the shape of underlying or overlying tissue.

The term "implantable" and derivatives thereof means the device can be inserted, embedded, grafted or otherwise acutely or chronically attached or placed in or on a subject.

The terms "winding" and "wound" and derivatives thereof means to wrap about an object or center at least once, typically repeatedly, e.g., to turn in a series of circular motions. In some embodiments, at least one collagen fiber (multiple fibers, one or more fiber bundles) turns or rotates its circumferential position about a centerline or long axis. The winding may define a coil (e.g., a series of connected typically substantially concentric rings or spirals), woven and/or braided fiber arrangement with a number of revolutions or turns about a core and/or tube, typically in a regular pattern (but an irregular pattern may also be used) about a length of at least one layer of a tube or cylindrical shape.

The present invention finds use in medical applications and animal studies. The term "medical" includes both human and veterinary uses. Suitable subjects of the present invention include, but are not limited to avians and mammals.

In particular embodiments, the subject is "in need of" the methods of the present invention, e.g., the subject may benefit from a surgical procedure implanting a collagen construct of the present invention, such as a prosthesis or other device. In certain embodiments, after implantation, the collagen constructs of the present invention can confer a therapeutic and/or prophylactic effect to the subject, such as prevent a disease and/or clinical symptom, reduce the severity of a disease and/or clinical symptom relative to what would occur in the absence of the methods of the prevent invention, and/or delay the onset and/or progression of a disease and/or clinical symptom. The methods of the present invention can provide complete and/or partial treatment and/or protection. In particular embodiments, after implantation in a subject, the collagen constructs of the present invention treat and/or inhibit and/or protect against a microbial infection in the subject.

Methods

In some embodiments, a method of manufacturing a medical construct is provided. The method comprises: providing a construct with biologically compatible polymer, contacting the biologically compatible polymer with chelating moieties to chemically bind the chelating moieties to the biologically compatible polymer and to provide a polymer-chelator conjugate, and chelating the polymer-chelator conjugate with a pharmacologically active metal ion, thereby producing a medical construct with an incorporated pharmacologically active metal ion. Suitable biologically compatible polymers, chelating moieties and pharmacologically active metal ion are as described herein.

The conjugates of this invention have broad therapeutic properties due to the localized and sustained released of a biologically active metal ion. In the case of silver ions, those biologically active ions can be used to treat wounds which are infected or at risk of infection by bacteria including antibiotic resistant bacteria such as methicillin-resistant *staphylococcus aureus* infections. Therapeutic copper ions are useful in the treatment of patients infected with or at risk of infection with fungal infections. Therapeutic platinum ions are useful in the treatment of cancer especially solid mass cancers.

EXAMPLES

Example 1

Preparation of a Collagen-Conjugate (A) Commerically available 2,3-dihydroxybenzoic acid (10 mmol) is converted to the corresponding methyl carboxylate by conventional methods. The hydroxyl groups of the methyl 2,3-dihydroxybenzoate then are protected by conversion to the corresponding benzyl ethers by reaction with at least 2 equivalents of benzyl bromide in acetone or N,N-dimethylformamide in the presence of an excess of potassium carbonate which scavenges the acid generated. The resulting methyl 2,3-dibenzyloxy benzoate is hydrolyzed and converted to the corresponding activated ester which in this case is the pentafluorophenyl ester using conventional techniques.

At least 30 equivalents of the active ester described above is combined with collagen under conventional amide forming conditions to provide for a plurality of protected chelating moieties bound to the collagen. Hydrogenation yields the 2,3-dihydroxyphenyl moiety. The hydroxyl groups possess chelating properties.

Chelation of the biologically active metal ion is achieved by conventional addition of a suitable metal salt such as silver nitrate, silver acetate, copper acetate, cis-platin and the like. Sufficient salt is added to effect substantial chelation of the chelating moieties on the collagen.

Example 2

Preparation of Micronized Placental Tissue

Amnion/chorion tissue grafts used here to produce the micronized particles were produced by the process described in US 2008/0046095, which is incorporated by reference in its entirety. Tissue grafts (4 cm×3 cm) and two 9.5 mm steel grinding balls were placed in 50 mL vials and the vials subsequently sealed. The vials were placed in the Cryoblock, and the Cryo-block was placed in a Cryo-rack. The Cryo-rack was placed into a liquid nitrogen holding-Dewar flask. Tissue samples were subjected to vapor phase cooling for no more than 30-60 minutes. The Cryo-rack was removed from the Dewar flask, and the Cryo-block was removed from the Cryo-rack. The Cryo-block was placed into the Grinder (SPEX Sample Prep GenoGrinder 2010) and set at 1,500 rpm for 20 minutes. After 20 minutes had elapsed, the tissue was inspected to ensure micronization. If necessary, the tissue was placed back into the Dewar flask for an additional 30-60 minutes, and moved to the grinder for an additional 20 minutes to ensure sufficient micronization. Once the tissue was sufficiently micronized it was sorted using a series of American Standard ASTM sieves. The sieves were placed in the following order: 355 µm, 300 µm, 250 µm, 150 µm, and 125 µm. The micronized material was transferred from the 50 mL vials to the 355 µm sieve. Each sieve was agitated individually in order to thoroughly separate the micronized particles. Once the micronized particles were effectively separated using the sieves, the micronized particles having particle sizes of 355 µm, 300 µm, 250 µm, 150 µm, and 125 µm were collected in separate vials.

Example 3

Preparation of Tissue Grafts with Micronized Placental Tissue

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

A detailed description of reinforced placental tissue grafts is provided in U.S. Patent Application Ser. No. 61/683,699 filed Aug. 15, 2012 and entitled REINFORCED PLACENTAL TISSUE GRAFTS AND METHODS OF MAKING AND USING THE SAME which application is incorporated herein by reference in its entirety.

A detailed description of making and using micronized placental tissue and extracts thereof is provided in U.S. Patent Application Ser. No. 61/683,700 filed Aug. 15, 2012 and entitled MICRONIZED PLACENTAL TISSUE COMPOSITIONS AND METHODS OF MAKING AND USING THE SAME which application is incorporated herein by reference in its entirety.

Example 4

Cell Migration in the Presence of EpiFix®

Figure 3:
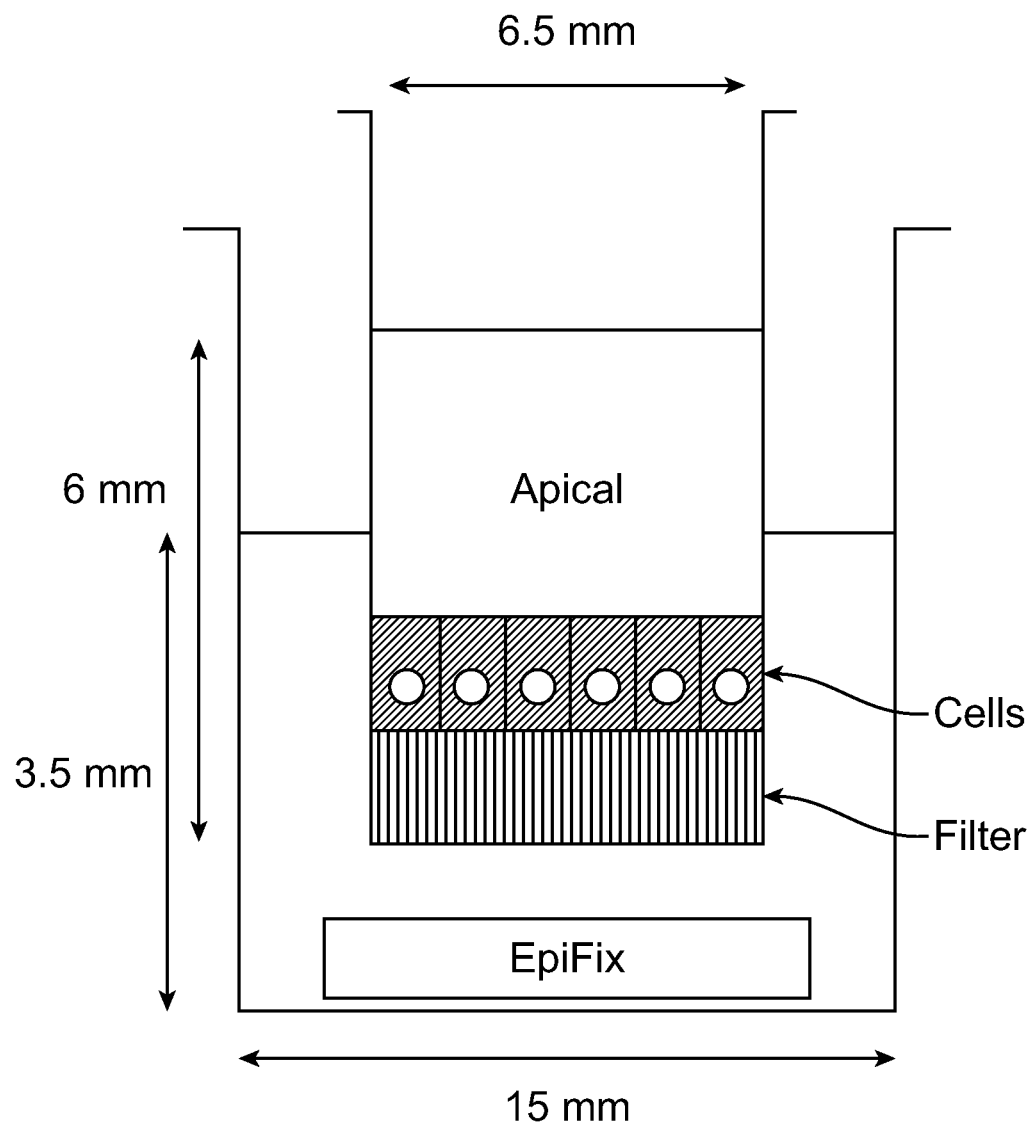
FIG. 3 shows a schematic for a cell culture insert for stem cell migration assays described in Example 4.

Human mesenchymal stem cells (human MSC) were evaluated in cell culture in the presence of samples of EpiFix® to determine whether the EpiFix® would induce migration of the human MSC. EpiFix® is a layer of amnion and chorion with the epithelial layer intact.
Materials and Methods Standard migration assays were performed in 24-well cell culture inserts with 8-µm pore membrane filters at the bottom of the insert (see FIG. 3; BD Biosciences). 24 hours prior to the start of the experiment, human MSCs (one donor, passage 3) were cultured in serum free media, and 300 µL of 5 µg/mL fibronectin in PBS was placed into each cell culture insert to enable adsorption of fibronectin to the cell culture insert surface overnight.

On the day of the experiment, 700 µL of serum-free culture medium was loaded into the bottom wells of the plate, followed by the addition of differently sized portions of sterilized EpiFix® (Low: 1.5-mm diameter disk; Medium: 4-mm diameter disk; High: 12×13 mm square, trimmed into 3-4 mm square pieces; n=6 EpiFix® tissue donors tested). One square centimeter of EpiFix® weighs 4 mg. Serum-free medium and medium with 10& fetal bovine serum (n=6) acted as negative and positive controls, respectively. Human MSCs (40,000 cells in 300 µL) were then loaded into the cell culture inserts and cultured for 24 hours. Then, both sides of the cell culture inserts were rinsed with PBS, and non-migrating cells in the upper portion insert were removed with a cotton-tipped applicator. Cells on the lower side of the insert plus the membrane filter were fixed in 10% formalin for 20 minutes, then rinsed and stained with hematoxylin for 5 min. The number of cells migrating through the membrane were counted on the lower surface of the membrane with an inverted microscope (Nikon TE2000; SPOT Software 4.6).

Figure 4:
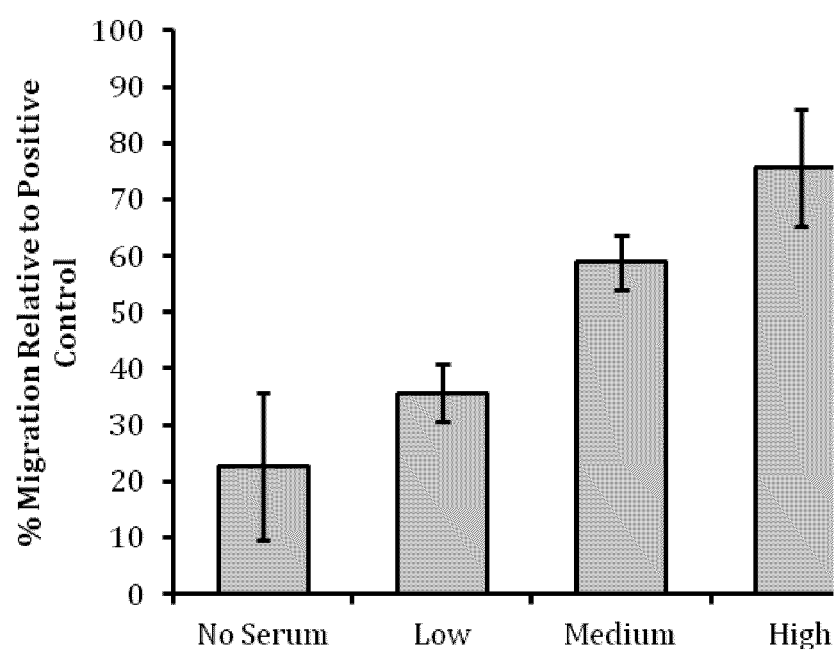
FIG. 4 shows a bar graph of percent cell migration in human mesenchymal stem cells (MSCs) cultured in the presence of various amounts of EpiFix®. Details are described in Example 4.

Data were normalized to the 10% FBS positive control and are expressed as mean±standard deviation of counted, migrated cells per 100× field micrograph for each sample well. Statistical comparisons were performed using a Box-Cox transformation to normalize data variance, followed by one-factor analysis of variance (ANOVA) with Tukey's honestly significant difference post-hoc test.
Results The Low group (1.5 mm diameter disk) containing the smallest EpiFix® sample was not significantly different from the no serum negative control (see bar graph in FIG. 4). Both the Medium group (4 mm diameter disk) and the High group (12×13 mm square, trimmed into 3-4 mm square pieces) were statistically higher than the no serum control (about 60% and 75% migration relative to control; see FIG. 4), indicating that EpiFix® stimulated cell migration. The High group was not significantly different from the Medium group. The results indicate that the EpiFix® product contains one or more factors that attract human mesenchymal stem cells.

Example 5

Stem Cell Recruitment in Mice Receiving EpiFix® Implants

A study was undertaken to determine whether EpiFix® implanted in normal mice causes recruitment of stem/progenitor cells, focusing on mouse hematopoietic stem cells (HSCs) and mouse mesenchymal stem cells (mouse MSCs).
Materials and Methods EpiFix® products from six donors were used for implantation in normal mice. A 5×5 mm square of EpiFix® was surgically placed subcutaneously in 4 month old FVB/NJ mice (weighing between about 23.50 g and about 30 g). Four mice were implanted per sample per time point. The time points were 3, 7, 14 and 28 days. The negative controls were normal skin and sham operated mice (surgical incision but no implant). Decellularized dermal matrix (acellular dermal matrix; ADM) was used as the comparative implant (Type I collagen, no cytokines). The implant and overlying skin was harvested for fluorescence-activated cell sorting (FACS).

Implants and overlying skin were harvested, cut into 1 mm² sections, and incubated in a 0.15% dispase/0.075% collagenase solution at 37° C. for 1 hour. After centrifugation, samples were stained with a lineage antibody cocktail as described below. CD31 antibody was added followed by Alexa Fluor 647 anti-rat secondary antibody. Phycoerythrin-Cy7-conjugated anti-CD45 antibody was incubated last. Samples were prepared and analyzed as described below.

Samples were incubated with a lineage negative (lin⁻) antibody cocktail (Ter119/CD4/CD8a/Gr-1/CD45R/CD11b) followed by phycoerythrin-Cy5 anti-rat secondary antibody. For mesenchymal stem cell analysis, conjugated antibodies were added against CD45 (phycoerythrin-Cy7) and Sca-1 (fluorescein isothiocyanate). For hematopoietic stem cell analysis, conjugated antibodies were added against CD45 (phycoerythrin-Cy7), c-Kit (phycoerythrin), and Sca-1 (fluorescein isothiocyanate). Samples were incubated with antibodies for 30 minutes and then washed by adding 5 volumes of 2% fetal bovine serum in phosphate-buffered saline with 2 mM ethylenediaminetetraacetic acid. Cells were centrifuged and then re-suspended in propidium iodide for 1 minute at 4° C. Samples were analyzed using an LSR Flow Cytometer. Using CellQuest software), samples were gated for lin-/Sca-1+/CD45- to define mesenchymal stem cells and for lin-/Sca-1+/c-Kit+/CD45+ to define hematopoietic stem cells.

Results

Figure 5A:
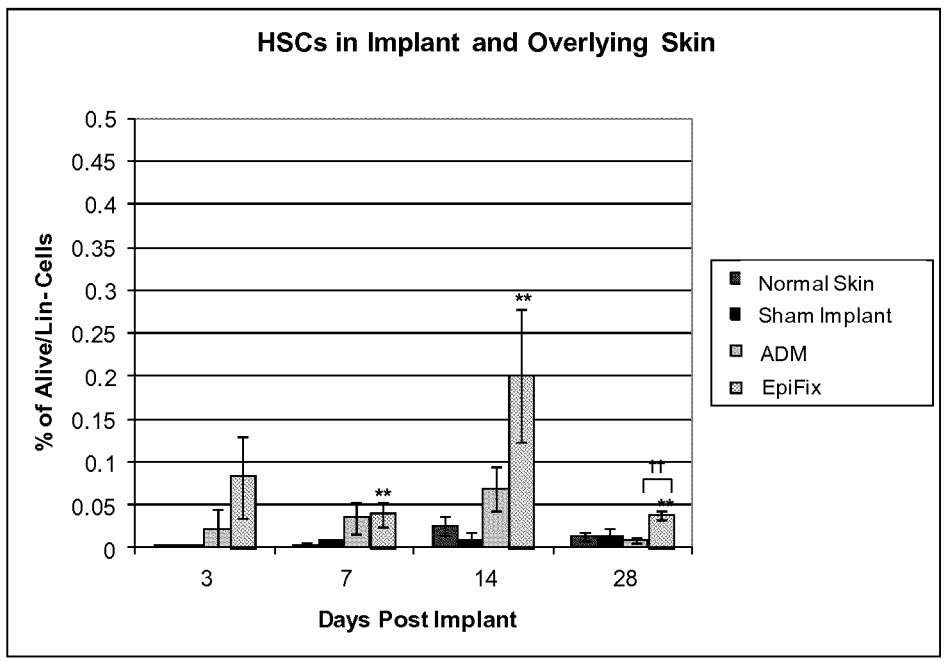
FIG. 5A shows a bar graph of percentage living/Lin⁻ mouse hematopoietic stem cells in normal skin, sham implant, acellular dermal matrix, and EpiFix® at 3, 7, 14, and 28 days post implant. Values shown are means+/−standard deviation, n=4 specimens.  indicates $p<0.05$ when comparing EpiFix® or control ADM to normal skin and sham implant via one-way ANOVA. †† indicates $p<0.05$ when comparing EpiFix® to control ADM via two tailed t-test.

Mouse HSCs were significantly increased following EpiFix® implantation compared to negative controls at days 7, 14 and 28 (see FIG. 5A). Mouse HSCs remained significantly increased in the EpiFix® samples at day 28 compared to ADM.

Figure 5B:
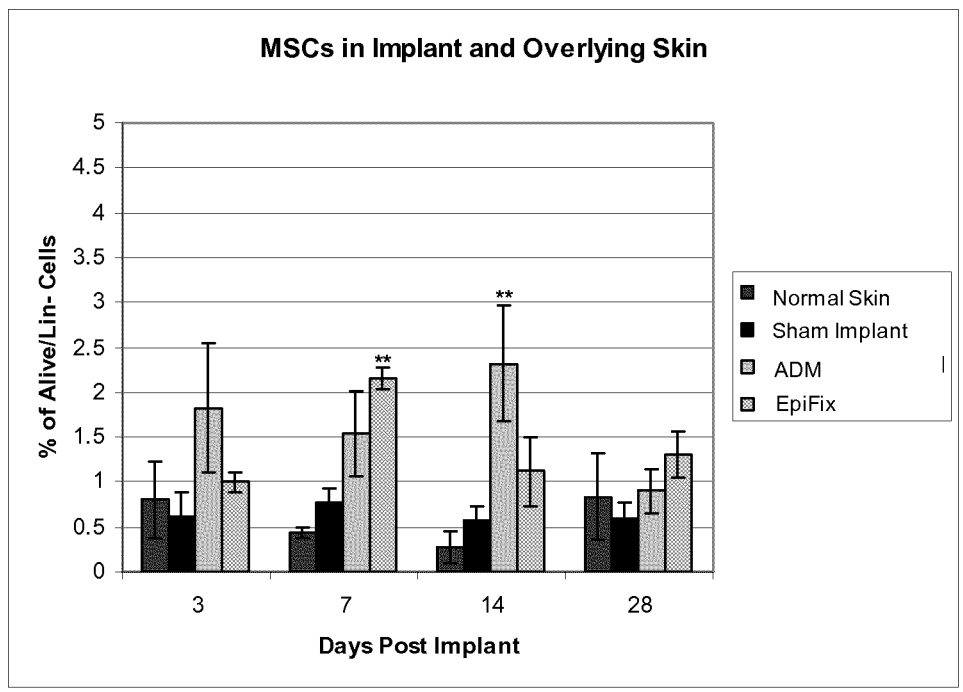
FIG. 5B shows a bar graph of percentage living/Lin⁻ mouse mesenchymal cells in normal skin, sham implant, acellular dermal matrix, and EpiFix® at 3, 7, 14, and 28 days post implant. Values shown are means+/−standard deviations, n=4 specimens.  indicates $p<0.05$ when comparing EpiFix® or control ADM to normal skin and sham implant via one-way ANOVA. Details are described in Example 5.

Mouse MSCs were significantly increased following EpiFix® implantation compared to negative controls at day 7 (see FIG. 5B). The average percentages of mouse MSCs were increased at all time points compared to negative controls.

Thus the data described above show that EpiFix® implants effectively recruit both HSCs and MSCs in vivo in normal mice. The data also show that EpiFix® leads to longer term HSC recruitment than acellular dermal matrix (ADM), supporting the hypothesis of a cytokine mediated effect of EpiFix®.

Example 6

Stem Cell Characterization in Mice Receiving EpiFix® Implants

A study was undertaken to characterize stem cells recruited to EpiFix® implantation sites in mice, using flow cytometry and immunohistochemistry.

Materials and Methods

Sterile, Purion® processed EpiFix® in a 5×5 mm square patch was implanted subcutaneously through a skin incision on the backs of sixteen 4 month old FVB/NJ mice. Identical skin incisions were made in another sixteen mice to function as a control treatment (sham). For comparison with a collagen scaffold, a 5×5 mm square patch of decellularized human dermis (acellular dermal matrix; ADM) was implanted subcutaneously on the backs of sixteen mice. Un-operated mice were used as a source of "normal" back skin for the analyses.

The surgical site was removed at 3, 7, 14 and 28 days following implantation for analyses of stem cells. Four animals/group were used at each time point. Stem cells were identified with two distinct methods: Fluorescence-activated cell sorting (FACS) and immunohistochemistry (IHC). For the FACS analysis, all cells were isolated from the amnion and associated regenerated tissue. The cells were fluorescently labeled with antibodies to specific stem cell markers. The identity and number of each cell type were determined with a flow cytometer.

For the immunohistochemical analyses, the membrane and associated regenerated tissue was fixed, sectioned for slides, and stained with specific antibodies to stem cells. Two antibodies were used for the immunohistochemistry: anti-CD34, which specifically detects hematopoietic progenitor cells (HPC), and reacts with dermal progenitor cells, endothelial cells, dendritic cells; and anti-CD31, which detects endothelial cells. The stained tissue sections were examined microscopically and the presence and number of specific stem cell types were measured. For the experimental analysis, the relative number of each cell type was counted. The results were calculated as the percentage of each cell type (no. of immunostained cells/total number of cells). Two areas were analyzed immunohistochemically for cell recruitment: the tissue surrounding the implant and the implant itself.

Results

Figure 6A:
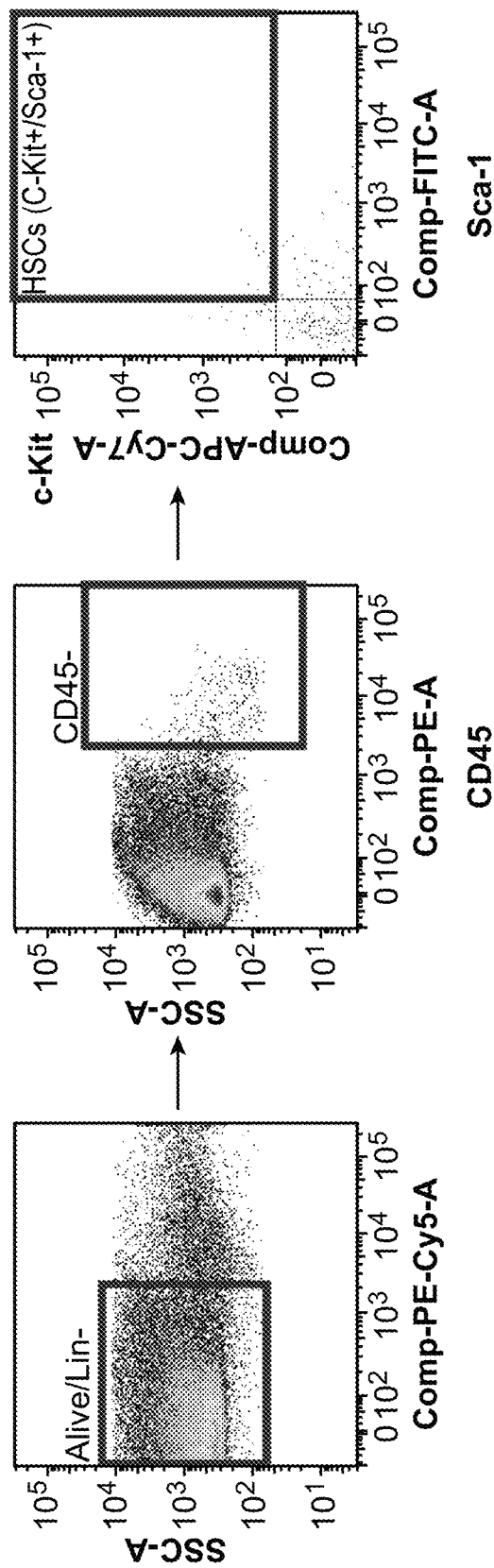
FIG. 6A shows representative FACS dot plots of cells detected using flow cytometry and fluorescent detection of CD45 and Sca-1.

Representative data from the FACS analyses are shown in FIG. 6A. The left panel shows the total number of cells in the sample. The middle panel shows the number of CD45 positive cells (in red box). The right panel shows the number of Sca-1 positive cells (in red box). CD45 and Sca-1 are specific markers for hematopoietic stem cells.

Figure 6B:
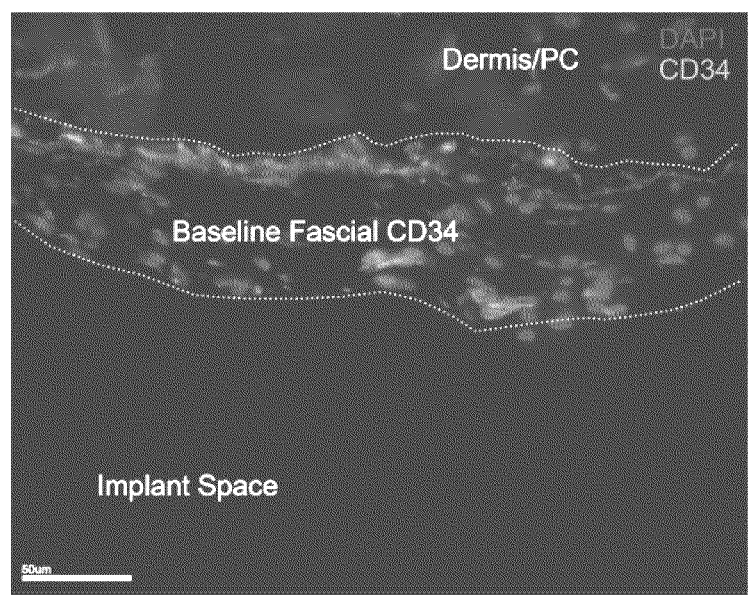
FIG. 6B shows photomicrograph of dermal tissue stained with DAPI which stains cell bodies, and CD34, which is a marker for hematopoietic stem cells. Details are described in Example 6.

FIG. 6B shows an exemplary immunohistochemistry image. The gray bar in the lower left corner represents 50 µm. The section was stained with DAPI (blue—stains all cells) and anti-CD 34 (red). The place where the tissue is implanted in the experimental mice is shown for reference.

Hematopoietic progenitor cell (HPC) levels were significantly elevated in tissue surrounding EpiFix® implants at days 14 and 28 compared to negative controls. Hematopoietic progenitor cells were significantly increased in the tissue surrounding the EpiFix® implant at days 14 and 28 compared to collagen scaffold ADM control.

Progenitor cells were recruited into the EpiFix® implant. Intra-implant hematopoietic progenitor cells peaked at day 14 in the EpiFix® implant, and remained elevated at day 28. Average intra-implant hematopoietic progenitor cells were increased in the EpiFix® implant at days 14 and 28 compared to control ADM. Progenitor cells were not recruited into the ADM control implant.

Vascularization of the EpiFix® implant steadily increased from day 14 to day 28. The amount of new vessel formation in the EpiFix® implant was significantly greater than that in the ADM control on day 28.

These data establish that EpiFix® contains one or more factors that recruit both hematopoietic stem cells and mesenchymal stem cells to the site of injury. More of these stem cells were found in the EpiFix® membrane and associated regenerated tissue that in the sham or, more importantly, the control collagen scaffold. EpiFix® was significantly more effective than the control decellularized collagen scaffold in recruiting progenitor cells to colonize the implant site. There were more progenitor cells in the EpiFix® membrane than in the control collagen scaffold.

EpiFix® also induced new blood vessel formation in the associated regenerated tissue and the EpiFix® membrane itself. Vascularization in the EpiFix® membrane was significantly higher than in the collagen scaffold control.

Example 7

Preparation of Non-Cross-Linked Tissue-Chelator Conjugates

Various placental tissue grafts described above were combined with at least 30 equivalents of dopamine under conventional amide forming conditions to provide for a plurality of protected chelating moieties bound to the placental tissue. The nitrogen of the dopamine reacts with a number of carboxylic acid groups of the amniotic collagen to form a carbodiamide linkage.

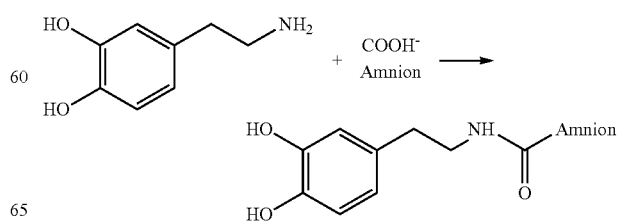

Example 8

Chelation of the Biologically Active Metal Ion with the Polymer Chelator Conjugate Dry non-cross-linked tissue-chelator conjugates described above are incubated in 1% (w/v) cis diamino Pt(II) diaqua salt in water at room temperature for 16 hours. The grafts are then washed with deionized water and dried. Platinum content in the conjugates is measured e.g., by Inductively Coupled Plasma-Mass Spectrometry (ICP-MS). Results are expressed as µg/g, which is equivalent to parts per million (ppm).

The incorporation of platinum in the conjugates can produce a biomaterial imbibed with anticancer capabilities. As such, the method of incorporating platinum into tissue materials can provide a drug delivery device, preferably for anticancer drug delivery.

In some embodiments, the tissues utilized in the conjugates of the present invention also incorporate one or more stem cell recruiting factors that enhance stem cell chemotaxis and or recruitment. Such compositions for recruiting stem cells are described in in U.S. patent application Ser. No. 13/815,873 filed Mar. 15, 2013 and entitled COMPOSITIONS AND METHODS FOR RECRUITING STEM CELLS which application is incorporated herein by reference in its entirety. These stem cell recruiting factors in combination with the biologically active metal are abhorrent to cancerous cells and work against tumor related recurrence of cancer.

It is evident from the above examples that the EpiFix® amniotic membrane allograft has the capability to attract or increase the flux of stem cells to the amnion. Thus, the amniotic membrane is a biologically derived polymer which attracts stem cells. Further, if the aminotic membrane is conjugated to the chelator moiety and a metal such as e.g, cisplatin, then the polymer conjugate can be used to kill stem cells, particularly aberrant stem cells such as tumor cells.

The invention claimed is:

1. A biologically compatible polymer-chelator conjugate comprising a biologically compatible non-cross-linked polymer and one or more chelating moieties selected from the group consisting of nordihydroguaiaretic acid (NDGA), 3,4-diyhydroxyphenylalanine, dopamine, 3,4-dihydroxybenzaldehyde, 3,4-dihydroxybenzoic acid, a precursor compound having the structure

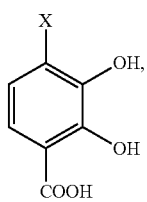

a precursor compound having the structure

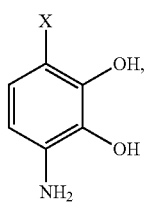

a precursor compound having the structure

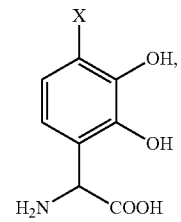

a precursor compound having the structure

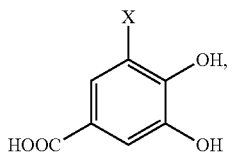

a precursor compound having the structure

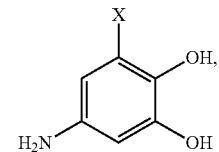

a precursor compound having the structure

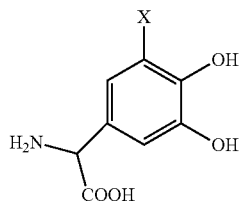

and a precursor compound having the structure

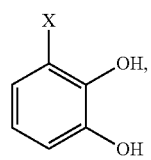

where X in each of said precursor compound structure is a complementary reactive functional group which covalently links said chelating moiety to said polymer, wherein the chelating polymer is non-cross-linked.

2. The conjugate of claim 1, wherein said conjugate is chelated with a pharmacologically active metal ion.

3. The conjugate of claim 2, wherein the pharmacologically active metal ion is selected from the group consisting of silver ions, copper ions and platinum ions.

4. The conjugate of claim 3, wherein the platinum ion is $Pt^{+2}$.

5. The conjugate of claim 3, wherein the ionic platinum is cis-platin.

6. The conjugate of claim 1, wherein the biocompatible non-cross-linked polymer is collagen.

7. The conjugate of claim 1, wherein the biocompatible non-cross-linked polymer comprises placental tissue.

8. The conjugate of claim 7, wherein the placental tissue comprises amnion or chorion.

9. The conjugate of claim 7, wherein the placental tissue comprises amnion.

10. The conjugate of claim 9, wherein the placental tissue has a mass sufficient to recruit stem cells to a body part to be treated.

11. A method of manufacturing a medical construct comprising:
providing a construct with a biologically compatible non-cross-linked polymer;
contacting the biologically compatible polymer with chelating moieties to chemically bind the chelating moieties to the biologically compatible non-cross-linked polymer and to provide a polymer-chelator conjugate, wherein the chelating moieties are selected from the group consisting of nordihydroguaiaretic acid (NDGA), 3,4-dyhydroxyphenylalanine, dopamine, 3,4-dihydroxybenzaldehyde, 3,4-dihydroxybenzoic acid, a precursor compound having the structure

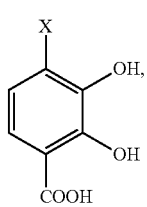

a precursor compound having the structure

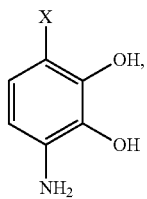

a precursor compound having the structure

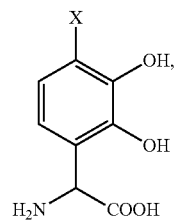

a precursor compound having the structure

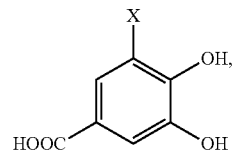

a precursor compound having the structure

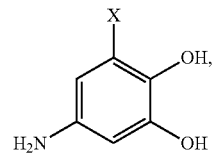

a precursor compound having the structure

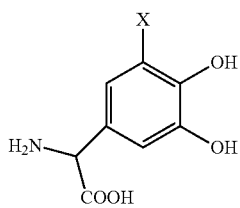

and a precursor compound having the structure

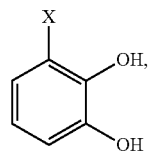

where X in each of said precursor compound structure is a complementary reactive functional group which covalently links said chelating moiety to said polymer, wherein the chelating polymer is non-cross-linked; and
chelating the polymer-chelator conjugate with a pharmacologically active metal ion, thereby producing a medical construct with an incorporated pharmacologically active metal ion.

12. The method of claim 11, wherein the biocompatible non-cross-linked polymer is collagen.

13. The method of claim 11, wherein the pharmacologically active metal ion comprises cis-platin.

14. A method for treating cancer amenable to treatment with cis-platin, said method comprising contacting said cancer with a sufficient amount of the conjugate of claim 5.

* * * * *